United States Patent [19]

Ohtake et al.

[11] 4,293,643
[45] Oct. 6, 1981

[54] ROTARY SHAKING CULTURE MEASURING METHOD AND APPARATUS

[75] Inventors: Yukio Ohtake; Masahiro Nakamura, both of Tokyo, Japan

[73] Assignee: Ohtake Works Company, Ltd., Tokyo, Japan

[21] Appl. No.: 116,184

[22] Filed: Jan. 28, 1980

[30] Foreign Application Priority Data

Jan. 31, 1979 [JP] Japan .................................. 54-9174

[51] Int. Cl.³ ............................................. C12Q 1/06
[52] U.S. Cl. ..................................... 435/39; 366/142; 366/214; 435/32; 435/33; 435/40; 435/289; 435/291; 435/316; 435/34
[58] Field of Search ................. 233/26; 366/142, 143, 366/214; 356/426, 427, 36; 435/29, 32, 33, 34, 38, 39, 40, 287, 289, 291, 299, 300, 316, 808

[56] References Cited

U.S. PATENT DOCUMENTS

| | | | |
|---|---|---|---|
| 1,834,536 | 12/1931 | Schaut | 435/291 |
| 3,163,404 | 12/1964 | Kraft | 366/214 |
| 3,322,956 | 5/1967 | Shah | 435/808 X |
| 3,542,515 | 11/1970 | Scott | 435/291 X |
| 3,615,140 | 10/1971 | Doornekamp et al. | 356/427 X |
| 3,776,817 | 12/1973 | Van der Pfordten | 435/291 X |
| 3,819,271 | 6/1974 | Beug et al. | 356/427 X |
| 3,928,140 | 12/1975 | Wyatt et al. | 435/291 X |

FOREIGN PATENT DOCUMENTS 53-43588 11/1978 Japan .

*Primary Examiner*—Robert J. Warden
*Attorney, Agent, or Firm*—Jordan and Hamburg

[57] ABSTRACT

Rotary shaking culture measuring method and apparatus characterizes in that culture tubes are disposed radially and at equal intervals in the circumferential direction, and an inclined turntable is disposed at a predetermined angle of inclination with respect to a horizontal reference plane, a central shaft of the inclined turntable serves as a driving shaft whereby a turning motion in a continuous or intermittently indexing form is imparted to the turntable. In addition, the culture tubes revolve along an inclined circular orbit described by such turning motion, and the substance being cultured within the tubes is shaked and cultured by a reciprocative motion of inertial resultant force of centrifugal force and gravity. Furthermore, in a certain position of the turntable the growth of the substance being cultured within all the culture tubes is measured with the lapse of time by a signal obtained at every fixed cycle.

12 Claims, 4 Drawing Figures

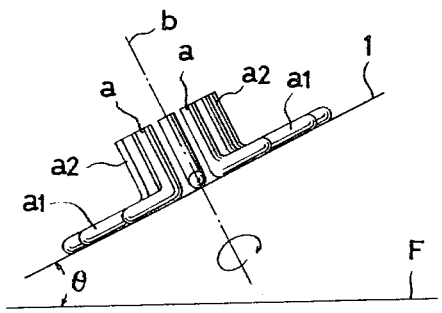
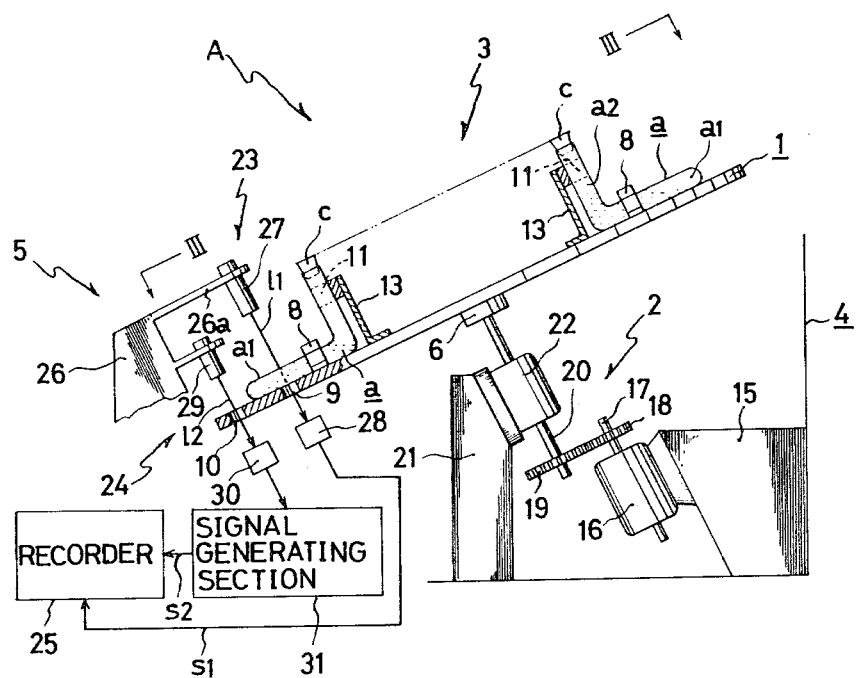

ROTARY SHAKING CULTURE MEASURING METHOD AND APPARATUS

This invention relates to a method and apparatus for measuring and recording, with the lapse of time, the degree of growth of various microorganisms while the latter are being shaked and cultured within many culture tubes.

For example, as a previous invention of this sort there is the invention entitled, "Method and apparatus for a continuous, automatic shaking culture" which was published under Japanese Patent Publication No. 43588/78. In the invention just cited, a photoelectric colorimeter is disposed at suitable places whereby the growth degree of bacteria within all test tubes can be measured at every fixed time. To this end, however, it is essential that the test tubes be moved cyclically along guide rails which form a zigzag closed loop. Furthermore, a reciprocable shaking bar provided at the lower portion of the guide rails strikes the lower part of a test tube to cause an arc motion with the upper part as fulcrum whereby the test tube is shaked. Such a construction inevitably requires larger-scaled and complicated equipment.

As can be seen from the above-cited invention, moreover, the conventional shaking means is to exert a striking force directly on the culture tube itself, but such a shaking operation can damage the culture tube; besides, the culture tubes are shaked one by one, so the shaking mechanism becomes very complex.

It is an object of this invention to provide a rotary shaking culture measuring method and apparatus in which culture tubes are disposed radially on an inclined turntable and are shaked by a turning motion of said turntable.

It is another object of this invention to provide a rotary shaking culture measuring method and apparatus developed on the basis of different shaking means from the prior art.

Other objects of this invention will become apparent by referring to this specification and the accompanying drawings, in which:

FIG. 1 illustrates the method of this invention;

FIG. 2 is a conceptual view of the apparatus of this invention;

To further illustrate the invention, reference is now made to FIG. 1.

Culture tubes, a, are disposed radially and at equal intervals in the circumferential direction, and an inclined turntable 1 is disposed at a predetermined angle of inclination, $\theta$, with respect to a horizontal reference plane F. A central shaft, b, of the inclined turntable 1 serves as a driving shaft whereby a turning motion in a continuous or intermittently indexing form is imparted to the turntable 1. The culture tubes, a, revolve along an inclined circular orbit described by such turning motion, and the substance being cultured within the tubes is shaked and cultured by a reciprocative motion of inertial resultant force of centrifugal force and gravity. Furthermore, in a certain position of the turntable 1 the growth degree of the substance being cultured within all the culture tubes, a, is measured with the lapse of time by a signal obtained at every fixed cycle.

Figure 3:
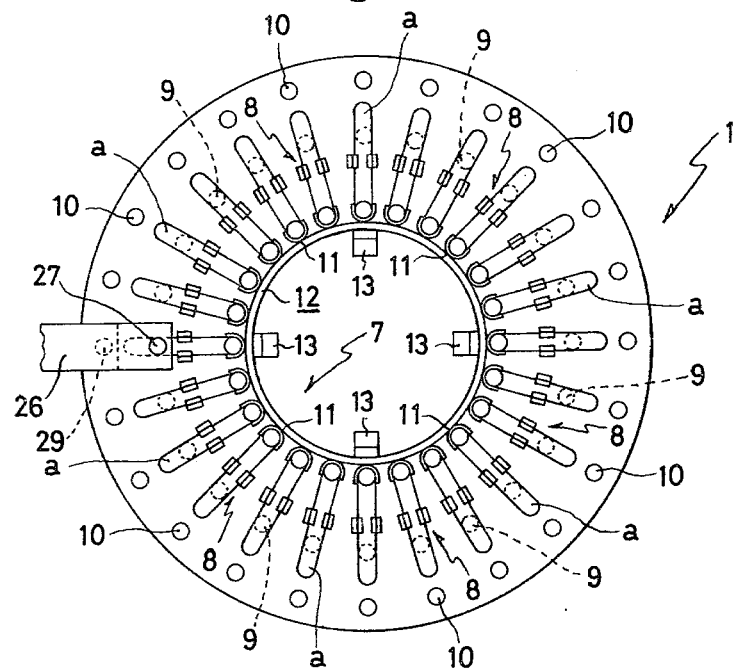
FIG. 3 is a plan view taken on line III—III in FIG. 2.
Figure 4:
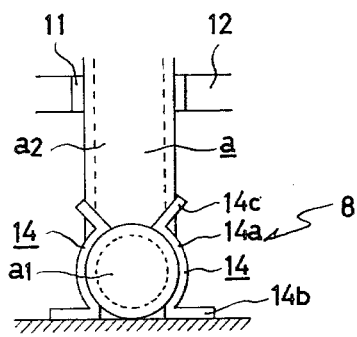
FIG. 4 illustrates a fixed state of culture tube.

Reference is now made to FIGS. 2 through 4 to illustrate an embodiment of an apparatus to which the method of this invention has been applied.

A rotary shaking culture measuring apparatus A acording to this invention comprises a shaking mechanism 3 mounted within a thermostatic oven 4, said shaking mechanism 3 supporting with a shaft an inclined turntable 1 capable of disposing thereon the culture tubes, a, radially at equal intervals and being equipped with a driving mechanism 2 whereby permitting the turntable 1 to turn freely, and a growth measuring device 5 disposed in close proximity to the turntable 1 and functioning to measure the ever-changing growth in the culture tubes, a.

The turntable 1 is disc-shaped as shown in FIG. 3, to the lower the central part of which is secured a shaft fixing ring 6, while in the intermediate area exclusive of central and outer peripheral portions on the upper surface is mounted a culture tube support 7 in the same circular form so as to permit the culture tubes, a, to be disposed and fixed radially at equal intervals, and also disposed in the said intermediate area are retaining means 8 which are provided by the number matching the number of the culture tubes, a. The culture tubes, a, are each L-shaped having a horizontal portion, a1, and a vertical portion, a2.

In predetermined positions of the inclined turntable 1 in contact with the lower surfaces of the horizontal portions, a1, of the culture tubes, a, which are disposed and fixed on the inclined turntable 1, there are formed therethrough concentration detecting holes 9 in the same circular form and at equal intervals, which holes 9 become opposed to the growth measuring device 5. Furthermore, synchronizing signal detecting holes 10 are formed through the turntable 1 also in the same circular form in positions close to the outer periphery thereof and on the same radial lines as the concentration detecting holes 9.

The number of culture tubes, a, to be disposed and fixed radially on the inclined turntable 1 may be set optionally on condition that the culture tubes, a, are disposed radially and at equal intervals. And according to the preset number of culture tubes there may be provided the culture tube support 7 or concentration detecting holes 9.

The culture tube support 7 consist of supporting pieces 11 secured to the outer peripheral wall of a ring 12 by the number corresponding to the number of culture tubes, a, disposed, and a total of four L-shaped supporting pillars 13 stood up on the inclined turntable 1 with their upper ends secured to the inner peripheral wall of the ring 12 at intervals of 90 degrees.

The retaining means 8 consists of a pair of retaining pieces 14, 14 each made up of an arc portion 14a matching the outside diameter of the horizontal part, a1, of the culture tube, a, a fixing portion 14b and an operation portion 14c which are bent outwards from the ends of the arc portion 14i a, the pair of retaining means 14, 14 being disposed in opposed relation so as to hold and fix the culture tube, a, therebetween. The retaining means 8 is formed of an expansible elastic material.

Thus the vertical portion, a2, of the culture tube, a, is, at an upper part thereof, fitted in and supported by the supporting piece 11 of the culture tube support 7, while the horizontal portion, a1, can be nipped and fixed firmly by the retaining means 8, and besides, the culture tubes, a, thus fixed in place can be removed extremely easily.

In the driving mechanism 2, a driving motor 16 is fixed to a motor fixing base 15, and on a motor shaft 17 of the driving motor 16 is mounted a driving gear 18, while a driven gear 19 in outer gearing with the driving gear 18 is mounted on the lower end of a driven shaft 20. The driven shaft 20 is journaled through a thrust bearing 22 which is fixed to a bearing fixing base 21, with the upper end of the driven shaft 20 being fitted in the shaft fixing ring 6 of the inclined turntable 1, and the driven shaft 20 and the inclined turntable 1 are integrally coupled together by suitable means.

Thus, the driving mechanism 2 may be of any construction if only a turning motion is imparted to the inclined turntable 1; for example, pulleys are fixed to the motor shaft 17 and driven shaft 20 and a belt (not shown) is stretched therebetween, or even the motor shaft 17 and the driven shaft 20 may be coupled together directly.

Accordingly, once the revolution of the inclined turntable 1 is set at a desired value, a continuous turning motion can be imparted to the inclined turntable 1 by the driving motor 16. If necessary, a step motor may be adopted for the driving motor 16 to generate an intermittent action with step control signals whereby an intermittently indexed revolution can be imparted to the inclined turntable 1.

The growth measuring device is composed of a photometer 23 for providing a measured concentration value signal, s1, a synchronizing signal gererator 24 for providing a synchronizing signal, s2, and a recorder 25 for recording on the basis of the signals, s1, and, s2, the growth of the substance being cultured within all the culture tubes, a, at every fixed cycle and with the lapse of time.

The photometer 23 includes a light sorce for concentration 27 which is fixed by utilization of an upper projection 26a of a mounting base 26 so as to be just above the concentration detecting holes 9 formed in the same circular form through the inclined turntable 1. The light source for concentration 27, the concentration detecting hole 9 and a photo detector 28 are disposed on the same optical axis so that a detecting light, 11, emitted from the source 27 passes through lens and filter (neither shown), then with the rotation of the inclined turntable 1, passes through the horizontal portion, a1, of the culture tube, a, and further through the concentration detecting hole 9, and thereafter is detected by the photo detector 28. The transmitted light detected by the photo detector 28 is subjected to photoelectric conversion and then fed to the recorder 25 as the measured concentration value signal, s1. In the embodiment shown, a special semiconductor luminous body which has been stabilized by an IC stabilizer is used for the light source for concentration 27, and a photoelectric converting silicon photocell is used for the photo detector 28.

The synchronizing signal generator 24 is constituted by a synchronizing light source 29 and a photo detector 30, disposed in opposed relation on the same optical axis, as well as a signal generating section 31 which generates the synchronizing signal, s2. As the inclined turntable 1 rotates, a synchronism light, 12, from the synchronizing light source 29 passes through the synchronizing signal detecting hole 10 and is detected by the photo detector 30, whereupon an electrical signal resulting from photoelectric conversion at photo detector 30 is fed to the signal generating section 31 from which is then provided the synchronizing signal, s2, to the recorder 25 and this signal is utilized as a timesharing control signal.

In the recorder 25, the measured concentration value signal, s1, which is concerned with the growth degree of the substance being cultured within the culture tube concerned and which is detected at every fixed cycle, is controlled by the synchronizing signal, s2, and then displayed in analog or digital form with the lapse of time.

In the apparatus A of this invention constructed as above, a specimen, a medium and a microorganism are fed into the culture tube, a, and, after applying an air-permeable cap, c, the culture pipes, a, are disposed and fixed on the inclined turntable 1. Then, the driving motor 16 is started, the inclined turntable 1 is set at a desired revolution, e.g. one revolution per minutes, and a continuous turning motion is imparted to the inclined turntable 1.

With such turning motion, the culture solution within the culture tube, a, becomes movable reciprocably and cyclically from the horizontal portion, a1, toward the vertical portion, a2, or vice versa, and this action is repeated. As a result, the culture solution itself is stirred without direction shaking of the culture tube, a, itself, and thus a shaking culture is effected.

Assuming that on the inclined turntable 1 are disposed 50 culture tubes, a, radially and at equal intervals in the circumferential direction, measured concentration value signals, s1, concerned with the degree of growth within the culture tubes, a, are obtained from the photometer 23 successively for example at every 1.2 seconds, and at the same time synchronizing signals, s2, are obtained from the synchronizing signal generator 24. And at every cycle of one minute, measured concentration value signals, s1, and synchronizing signals, s2, corresponding to 50 culture tubes, a, under measurement are fed to the recorder 25.

In other words, the measured concentration value signal, s1, from the same culture tube, a, is obtained at every minute, then controlled by the synchronizing signal, s2, which is simultaneously obtained, and at every minute is displayed in analog or digital form by the recorder 25.

Thus, with the measured concentration value signals, s1, obtained at every fixed cycle, the growth degree of microorganism within all culture tubes, a, under shaking culture can be observed with the lapse of time.

The above description is of the case where a continuous turning motion is imparted to the inclined turntable 1.

in case an intermittently indexed turning motion is imparted to the inclined turntable 1, the resulting action is basically the same as in the case of the aforesaid continuous turning motion imparted to the inclined turntable. So explanation is here omitted.

In this invention, as hereinabove described, a shaking culture is effected by imparting a turning motion to the culture tubes, a, which are disposed collectively on the inclined turntable 1, and further the shaking mechanism 3 is quite different in its basic construction from conventional ones. And while the shaking culture is continued by the turning motion of the inclined turntable 1, this turning motion makes the use of only one photometer 23 possible to obtain the measured concentration value signal, s1, at every fixed time whereby the degree of growth of microorganism can be observed with the lapse of time.

Consequently, not only the shaking mechanism 3, as compared with conventional ones, can be simplified and manufactured more easily, but also even in comparison with the conventional apparatus capable of handling the same number of specimens, saving in size can be attained.

If means capable of injecting specimen and medium and inoculating bacteria into the culture tube, a, is attached to the apparatus of this invention, the advantage of this invention will be further enhanced.

What is claimed is:

1. A rotary shaking culture measuring apparatus comprising a rotatable turntable means rotatable about an axis which is disposed at an acute angle relative to vertical, said turntable means comprising a turntable element rotatable in a plane generally perpendicular to said axis, a plurality of radially spaced culture means carried on said turntable means, said culture means each being generally L-shaped and each having an upright portion joined to a lateral portion, said upright portion being disposed generally parallel to said axis and said lateral portion being generally parallel to said turntable element such that upon rotation of said turntable means, said culture means is stirred by the resultant force of gravity and centrifugal force, retaining means retaining said culture means on said turntable means, said turntable element having a plurality of concentration detection openings, a concentration measuring device disposed adjacent to said turntable means comprising a light source and a light detector device operable in association with said concentration detection openings to provide a concentration signal indicative of the concentration in said culture means, and a synchronizing device disposed adjacent to said turntable means operable to detect passage of said culture means past a predetermined position and thereby provide a synchronization signal for synchronizing the measuring of said concentration by said concentration measuring device as said culture means pass successively by said concentration measuring device.

2. A rotary shaking culture measuring apparatus according to claim 1 wherein said turntable element is a disk member disposed generally in a plane perpendicular to said axis of rotation, said retaining means comprising upright supports extending upright from said disk member for supporting said upright portions of said culture means.

3. A rotary shaking culture measuring apparatus according to claim 2 wherein said retaining means further comprises mounting members on said disk member for mounting said lateral portions of said culture means on said disk member.

4. A rotary shaking culture measuring apparatus according to claim 1 wherein said retaining means are constructed and located to mount said culture means at radial spaced positions on said disk element and with said lateral portions of said culture means disposed generally parallel to said disk element and with said upright portions of said culture means disposed generally perpendicular to said disk element.

5. A rotary shaking culture measuring apparatus according to claim 1 wherein said concentration detection openings underlie each of said lateral portions of said culture means, said light source being disposed on one side of said turntable element and said light detector device being disposed on the opposite side of said turntable element in optical alignment with said light source such that said lateral portions of said culture means and the underlying associated concentration detection openings pass successively between said optically aligned light source and light detector device as said turntable means is rotated.

6. A rotary shaking culture measuring apparatus according to claim 1 wherein said turntable element has a plurality of synchronization openings in radial alignment with said concentration detection openings, said synchronizing device comprising a light source on one side of said turntable element and a light detecting device on the opposite side of said turntable element which is in optical alignment with said light source such that said synchronization openings pass successively between said optically aligned light source and light detecting device as said turntable means is rotated.

7. A rotary shaking culture measuring apparatus according to claim 1 wherein said turntable means comprises drive means for continuously rotating said turntable element.

8. A rotary shaking culture measuring apparatus according to claim 1 wherein said turntable means comprises drive means for intermittently rotating said turntable element.

9. A rotary shaking culture measuring apparatus according to claim 1 further comprising recording means connected to said concentration measuring device and to said synchronizing device for recording said concentration of said culture means.

10. A rotary shaking culture measuring apparatus according to claim 1 further comprising means defining an enclosure about said turntable means providing a closed and controlled atmosphere.

11. A rotary shaking culture measuring method comprising revolving a plurality of culture means about a fixed axis disposed at an acute angle relative to vertical and along an inclined circular path which is disposed at a right angle relative to said axis, said culture means each being L-shaped having an upright portion opening at the top thereof and a lateral portion, said upright portion being generally parallel to said axis, stirring the substance being cultured in said culture means by said revolutionary motion utilizing the reciprocative motion of the inertial resultant force of centrifugal force and gravity, continuously measuring the degree of growth of the substance being cultured within each said culture means when said culture means passes a predetermined position on said inclined circular path, said continuous measurement being effected by obtaining a concentration signal and a synchronizing signal at every cycle of revolution by light sources each passing a light through said culture means and through said inclined circular path respectively, said synchronizing signal detecting when each of said culture means passes said predetermined position and thereby providing timing for measuring said concentration, and indicating the concentration of said substance in analog or digital forms.

12. A rotary shaking culture measuring method according to claim 11 in which said revolving of said culture means is effected by rotating an inclined turntable which carries thereon said culture means.

* * * * *